United States Patent
Qazi et al.

(10) Patent No.: US 7,119,075 B2
(45) Date of Patent: *Oct. 10, 2006

(54) USE OF HERBAL AGENTS FOR POTENTIATION OF BIOEFFICACY OF ANTI INFECTIVES

(75) Inventors: Ghulam Nabi Qazi, Jammu & Kashmir (IN); Om Parkash Suri, Jammu & Kashmir (IN); Kasturi Lal Bedi, Jammu & Kashmir (IN); Inshad Ali Khan, Jammu & Kashmir (IN); Vijeshwar Verma, Jammu & Kashmir (IN); Rakesh Kamal Johri, Jammu & Kashmir (IN); Krishan Avtar Suri, Jammu & Kashmir (IN); Bishan Datt Gupta, Jammu & Kashmir (IN); Naresh Kumar Satti, Jammu & Kashmir (IN); Manoj Kumar Tikoo, Jammu & Kashmir (IN); Subhash Chander Sharma, Jammu & Kashmir (IN); Ashok Kumar Tikoo, Jammu & Kashmir (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/404,014

(22) Filed: Mar. 31, 2003

(65) Prior Publication Data
US 2004/0198672 A1    Oct. 7, 2004

(51) Int. Cl.
*A61K 31/70*    (2006.01)

(52) U.S. Cl. .................. 514/27; 514/359; 514/375; 514/449

(58) Field of Classification Search ............... 514/27, 514/359, 375, 449
See application file for complete search history.

(56) References Cited

U.S. PATENT DOCUMENTS

| 5,439,891 A | * | 8/1995 | Kapil et al. | .......... 514/31 |
| 5,665,386 A | * | 9/1997 | Benet et al. | .......... 424/451 |
| 5,744,161 A | * | 4/1998 | Majeed et al. | .......... 424/464 |
| 6,841,174 B1 | * | 1/2005 | Shalaby et al. | .......... 424/725 |

FOREIGN PATENT DOCUMENTS

| WO | 9714319 | 4/1997 |
| WO | 2004009061 | 1/2004 |

OTHER PUBLICATIONS

Hiwale, A. R., et al. "Effect of Co-Administration of piperine on Pharmacokinetics of beta-lactam antibiotics in rats" Database Biosis Online! Biosciences Information Service (2002) and Indian Journal of Experimental Biology, vol. 40, No. 3 (2002) pp. 277-281.

* cited by examiner

*Primary Examiner*—Elli Peselev
(74) *Attorney, Agent, or Firm*—Ladas and Parry LLP (57) ABSTRACT

The present invention relates to the use of bioenhancers to decrease the resistance of microbial strains to anti-infective such an antibiotics and antifungals by potentiating the activities of anti-infective. This may be useful to reduce resistance in bacteria and yeast to aid in the treatment of certain infections and disease and to lower the concentration of antiinfectives necessary to inhibit the growth of microbial strains.

26 Claims, 3 Drawing Sheets

Fig 1

Standard drug conc. µg/ml

USE OF HERBAL AGENTS FOR POTENTIATION OF BIOEFFICACY OF ANTI INFECTIVES

FIELD OF THE INVENTION

The present invention relates to the field of chemotherapeutics, particularly to their formulation as of oral pharmaceutical compositions containing bioenhancers for increasing bioefficacy of anti-infectives and thereby requiring lower doses and/or decreased frequency of dosing of such anti-infectives while maintaining the therapeutic efficacy of standard doses of such drugs.

BACKGROUND OF THE INVENTION

A variety of human ailments owe their origin to pathogenic microorgnisms, which include bacteria, virus and fungi. The presence of such pathogenic microorgnisms lead to septicaemia, serious infections of upper and lower respiratory tract, CNS, meningitis, intra-abdominal including peritoneum, genito-urinary tract, skin, and soft tissue, and variety of other infections like systemic mycosis, candidiasis including infections caused by dermatophytes. During the last 100 years, significant progress has been made to combat the diseases caused by such a large family of microbes with innumerable therapeutic agents of diverse chemical and biological nature that have become available as a short and long-term cure. Such antimicrobials include aminoglycosides, penicillins, cephalosporins, macrolides, glycopeptides, fluoroquinolones, tetracyclins, first and second line anti-TB drugs, anti-leprosy, antivirals, polyene, txiazole, and imidazole anti-fungals, combinations like pyrimidine derivatives and trimethoprim and sulphamethoxizole.

While such agents are effective against pathogenic bacteria and fungi and therefore useful in the treatment of disease conditions associated with the presence of such pathogens, there is increasing evidence that use of such agents has certain limitations and led to clinical concern. There are several such factors responsible for such a concern: (a) certain strains of bacteria and fungi become increasingly resistant to one or more of the known anti-infectives and therefore the usual or standard therapeutic doses lead to less beneficial effect, (b) higher doses that are required to combat this cause undesirable side effects and toxicity, and (c) high-cost of treatment and patient-non-compliance. The emergence of drug-resistant pathogenic organisms has also been attributed to uncontrolled antibiotic overuse and under use and even under dosing, irrational frequency of administration. The prolonged and high dose therapy is also a matter of serious concern particularly in pregnant women, geriatrics and children.

While an approach embodying rational use of antibiotics use may help slow the problem of microbial drug resistance, new antimicrobial agents must be discovered to combat those strains that are now resistant to most, if not all, currently available antibiotics. As such, there is a continued interest in the identification of novel antimicrobial agents, which can be used to further supplement the medical practitioner's armamentarium against pathogenic microorganisms In another approach, two anti-infectives are combined in such a way that the combination produces synergy i.e. one of the anti-infective acts as the potentiator of the other antiinfective. The example of such combination is Trimethoprim-sulfamethoxazole also known as co-trimoxazole or TMP-SMX, which was introduced in 1968 as a broad-spectrum antimicrobial agent. Trimethoprim was specially developed as a potentiator of sulphonamide to act synergistically against bacteria and delay the development of bacterial resistance. The 1:5 ratio of trimethoprim to sulfamethoxazole achieves an approximate 1:20 ratio of peak serum concentrations which is the optimal synergistic ratio of serum concentrations against most susceptible bacteria (Gutman L T, *Pediatr Infect Dis* 1984;3:349–57, Olin B R, *Facts and Comparisons, Inc.* 1998; 408b–409d, Cockerill F R, Edson R S, *Mayo Clin Proc* 1991;66:1260–9)

The combination can also be between one antiinfective agent and another chemical agent which by itself is not antiinfective in nature but when combined with the antiinfective, enhances the effectiveness of this antiinfective. The example of such combination is Amoxicillin+Clavulanic acid, more commonly known as Augmentin. Amoxicillin is an antibiotic of the penicillin type. It is effective against different bacteria such as *H. influenzae, N. gonorrhea, E. coli, Pneumococci, Streptococci*, and certain strains of *Staphylococci*. Chemically, it is closely related to penicillin and ampicillin. Addition of clavulanic acid to amoxicillin in Augmentin enhances the effectiveness of this antibiotic against many other bacteria that are ordinarily resistant to amoxicillin. Clavulanic acid is produced by the fermentation of *Streptomyces clavuligerus*. It is a β-lactam structurally related to the penicillins and possesses the ability to inactivate a wide variety of β-lactamases by blocking the active sites of these enzymes. Clavulanic acid is particularly active against the clinically important plasimd mediated β-lactamases frequently responsible for transferred drug resistance to penicillins and cephalosporins.

One of the most notable features that has been associated with the traditional Indian medicine and amply described in Ayurveda is the use of compositions which offer additive, synergistic and potentiating effect of one medicament when used in combination with the other. In Ayurveda there are several natural products, which have been used as an essential ingredient of many formulations used against wide range of diseases. The most prominent of these being 'Trikatu' comprising black pepper, long pepper and dry ginger. Detailed and systematic studies have shown that one of the active ingredients of peppers i.e., piperine is a potent bioavailability and/or bioeffacicay enhancer of several drugs and nutrients. The process of obtaining piperine and piperine containing formulations including anti-TB antibiotics with enhanced bioavailability/bioefficacy at lower doses of active drugs has been disclosed in earlier patents (IP 172684,; IP 172690,; IP 176433; U.S. Pat. No. 5,439,891).

OBJECTS OF THE INVENTION

The main object of the invention is to provide a oral pharmaceutical compositions containing bioenhancers for increasing bioefficacy of anti-infectives and thereby requiring lower doses and/or decreased frequency of dosing of such anti-infectives while maintaining the therapeutic efficacy of standard doses of such drugs.

SUMMARY OF THE INVENTION

The present invention deals with one such combinations, where piperine and other bioenhancers are used as potentiators when combined with various anti-infective agents in vitro using bacteria, viruses and yeast and in vivo using mice and guinea pig infection models. The present invention is aimed to overcome or avoid problems faced in the prior art. The use of products of the present invention offer a low dose regimen that produces enhanced therapeutic action comparable to that of standard dose alone.

Accordingly, the present invention provides a composition useful for enhanced therapeutic effect at reduced doses of the anti infectives against infection caused bya microorganism comprising a mixture of an anti-infective agent and a bioenhancer selected from piperine of formula 1 and 3',5-Dihydroxy flavone 7-O-β-D-galacturonide-4'-O-β-D-glucopyranoside of formula 2 or a mixture thereof.

The present invention also provides a process for the preparation of a composition useful for enhanced therapeutic effect at reduced doses of the anti infectives against infection caused bya microorganism comprising a mixture of an anti-infective agent and a bioenhancer selected from piperine of formula 1 and 3',5-Dihydroxy flavone 7-O-β-D-galacturonide-4'-O-β-D-g of formula 2 or a mixture thereof, said process comprising a physical admixing technique.

Formula 1

Formula 2

In one embodiment of the invention, the anti infective agent is selected from the group consisting of penicillins including semi synthetic, cephalosporins, aminoglycosides, glycopeptides, fluroquinolones, macrolides, tetracyclines, first and second line anti-TB drugs, antileprosy drugs, oxazolidelones, antifungal agents, antiviral agents and pyrimidine derivatives—sulphonamides combination.

In a further embodiment of the invention, the anti-fungal agent is selected from the group consisting of polyenes, imidazoles and triazoles.

In yet another embodiment of the invention, the antiviral agent is selected from the group consisting of Zidovudines, idouridine, acyclovir and ribavarine.

In another embodiment of the invention, the 3',5-Dihydroxy flavone 7-O-β-D-galacturonide-4'-O-β-D-glucopyranoside is used in pure form or in the form of a HPLC fingerprinted fraction of 3',5-Dihydroxy flavone 7-O-β-D-galacturonide-4'-O-β-D-glucopyranoside from *Cuminum cyminum* or a sub fraction.

In another embodiment of the invention, the concentration of the anti infective is two to eight times lesser than when such anti infective is used without the bioenhancer.

In another embodiment of the invention, the composition includes one or more pharmaceutically acceptable additives and excipients.

In another embodiment of the invention, the additives/excipients are selected from the group consisting of nutrients comprising proteins, carbohydrates, sugar, talc, magnesium stearate, cellulose, calcium carbonate, starch-gelatin paste, and/or pharmaceutically acceptable carriers, diluents and solvents.

In another embodiment of the invention, the composition is in oral administration form.

In a further embodiment of the invention, the ratio of the anti-infective to the bioenhancer is in the range of 1:1 to 1:5.

In yet another embodiment of the invention, the additives have no effect on the antiinfective property of the said composition.

In one embodiment of the invention, the physical admixing technique is selected from dialysis, molecular sieving and by membranes.

In another embodiment of the invention, the process of preparation of the bioenhancer comprises use of water, alcohol, combinations of water and alcohol, hydrocarbons, ketones and ethers.

In one embodiment of the invention, the anti infective agent is selected from the group consisting of penicillins including semi synthetic, cephalosporins, aminoglycosides, glycopeptides, fluroquinolones, macrolides, tetracyclines, first and second line anti-TB drugs, antileprosy drugs, oxazolidelones, antifungal agents, antiviral agents and pyrimidine derivatives—sulphonamides combination, In a further embodiment of the invention, the anti-fungal agent is selected from the group consisting of polyenes, imidazoles and triazoles.

In yet another embodiment of the invention, the antiviral agent is selected from the group consisting of Zidovudines, idouridine, acyclovir and ribavarine.

In another embodiment of the invention, the 3',5-Dihydroxy flavone 7-O-β-D-galacturonide-4'-O-β-D-glucopyranoside is used in pure form or in the form of a HPLC fingerprinted fraction of 3',5-Dihydroxy flavone 7-O-β-D-galacturonide-4'-O-β-D-glucopyranoside from *Cuminum cyminum* or a sub fraction.

In another embodiment of the invention, the concentration of the anti infective is two to eight times lesser than when such anti infective is used without the bioenhancer.

In another embodiment of the invention, the composition includes one or more pharmaceutically acceptable additives and excipients.

In another embodiment of the invention, the additives/excipients are selected from the group consisting of nutrients comprising proteins, carbohydrates, sugar, talc, magnesium stearate, cellulose, calcium carbonate, starch-gelatin paste, and/or pharmaceutically acceptable carriers, diluents and solvents.

In another embodiment of the invention, the composition is in oral administration form.

In a further embodiment of the invention, the ratio of the anti-infective to the bioenhancer is in the range of 1:1 to 1:5.

In yet another embodiment of the invention, the additives have no effect on the anti-infective property of the said composition.

DETAILED DESCRIPTION OF THE INVENTION

Bioefficacy/Bioavailability

Studies originating from the laboratory of the inventors resulted in conceptualisation of 'bioenhancers' wherein such agents, which by themselves are not therapeutic entities but when combined with an active drug lead to the potentiation of the pharmacologic effect of the drug. Such formulations have been found to increase the bioavailability/bioefficacy of a number of drugs even when reduced doses of drugs are present in such formulations. Evidence have been obtained for such classes of drugs which are (a) poorly bioavailable and/or efficacious, (b) require prolonged therapy, and (c) are highly toxic and expensive. For example, Patent Nos. IP 172690, IP 176433 and U.S. Pat. No. 5,744,161 disclose such art. Further studies carried out in the laboratory of the inventors have shown that such bioenhancers are not only capable of increasing bioavailability of a wide variety of therapeutic agents but are also capable of enhancing bioefficacy through a variety of mechanisms underscored in serial nos (a) to (g) below. As a result newer understanding has emerged about the factors involved in decreased cellular concentrations of drugs at which they fail to attain therapeutic levels and the strategies that make it possible to enhance the bioavailability and/or bioefficacy of these active drugs even at lower concentrations compared to standard high dosing. Some of these factors are:

(a) Increasing the penetration or entry of the active drug into the pathogen even where they become persistors, besides inhibiting the capability of pathogens and abnormal tissues to reject the drug. This would eventually ensure the enhanced killing of the pathogenic microorganisms, which are otherwise inaccessible to the active drug.

(b) Chemoresistance is a major problem in drug therapy. The mechanisms underlying the clinical phenomena of de novo and acquired drug resistance may arise from alterations at any step in the cell-killing pathway. These include drug transport, drug metabolism, drug targets, cellular repair mechanisms and the ability of cells to recognize a harmful toxin or pathogen. A common mechanism of reduced cellular drug accumulation is the increased expression of P-glycoprotein, a membrane transporter that efficiently removes drugs from these cells. Another limiting factor is the high activity of cytochrome P 450 dependent proteins. Both these proteins P-gp and CYP 450 have been shown to regulate the oral bioavailability of a majority of drugs. P-gp is considered to be associated with MDR caused by the levels of its expression in tumors and after drug therapy.

(c) Modifying the signalling process to ensure increased accessibility of drugs to the pathogens. Considerable evidence is accumulating to suggest that calcium signalling plays a major role in the therapeutic action of several drugs, which are effluxed by P-gp independent pathways. (Vilpo et al, *Haematologica* 2000:85:806–813). cAMP mediated signal pathways on the other hand are associated with an alteration in membrane fluidity (Friedlander G et al, *Biochimica et Biophysica Acta* 1990; 1022:1–7).

(d) Immunological intervention through NO production, CMI and/or humoral immune potentiation with favourable influence on the Th 1/Th 2 balance.

(e) Sensitization of specific receptors like proteins, DNA, RNA etc thus potentiating and prolonging the effect leading to enhanced antibiotic activity aghast pathogens, and disorders Adequate experimental evidences have been gained in respect of several of these mechanisms. For example, piperine has been shown to intercalate deeply into the phospholipids of the cell membrane, (Ray et al, *Ind. J Biochem. Biophys* 1999; 36: 248–251) modulating the membrane fluidity, which may alter the activity of membrane bound transporter proteins. The overall permeability changes may affect (i) specific ion transporter channels, and (ii) also lead to bulk movement of lipophilic solutes along the paracellular pathway. Such membrane changes have also been evidenced in the action of several polyene antibiotics (Milhaud J et al, *Biochimica et Biophysica Acta,* 1988; 943:315–325). However, the changes caused by piperine in membrane fluidity are, as already stated, short living, completely reversible but more than any thing is selective. Had it not been so, serious side effects and toxicity should have manifested themselves during phase II and phase III clinical trials of reduced dose formulation of anti-TB drugs wherein piperine was admisistered daily for six months at 10 mg dose vis-à-vis standard dose anti-TB drugs without piperine. The black pepper containing piperine is a part of food practically all over the world. The average amount of pepper consumed per capita will account for piperine content much more than the amount used in these formulations of present invention.

(f) Potentiating the mechanism of action of drugs and thus increasing their efficacy at lower doses e.g. inhibition of RNA polymerase transcription leading to potentiation of the effect of rifampicin at less than half the standard dose.

(g) Enhancing the absorption and/or inhibiting biotransformation of drugs thereby increasing bioavailability of drugs.

The products of the present invention are novel mechanism based pharmaceutical entities acting through synergism and or additive effect so that drugs contained in the formulation are more bioefficaceous as a result of one or more of the mechanism as revealed above and thereby increasing the sensitivity of the target cell to an anti-infective.

Description of the Formulations Containing Bioenhancer

The 'drug' in the present invention refers to a chemical entity capable of affecting organism's patho-physiology and used for the treatment or prevention of disease. Drugs include a number of classes of compounds, but not limited to aminoglycoside, penicillins, cephalosporins and other β-lactam agents, macrolides, glycopeptides, fluoroquinolones, tetracyclines, first and second line anti-TB drugs, antileprosy, antivirals, polyene, triazole, and imidazoles and combinations like pyrinidines, sulphamethoxazole. Drugs may be a pro-drug, activated or metabolised form, consisting of charged, uncharged, hydrophilic, hydrophobic or zwitterion species which make their entry by simple diffusion, carrier mediated transport dependent and not dependent on energy requirements, through ion and/or voltage gated channels.

Figure 1:
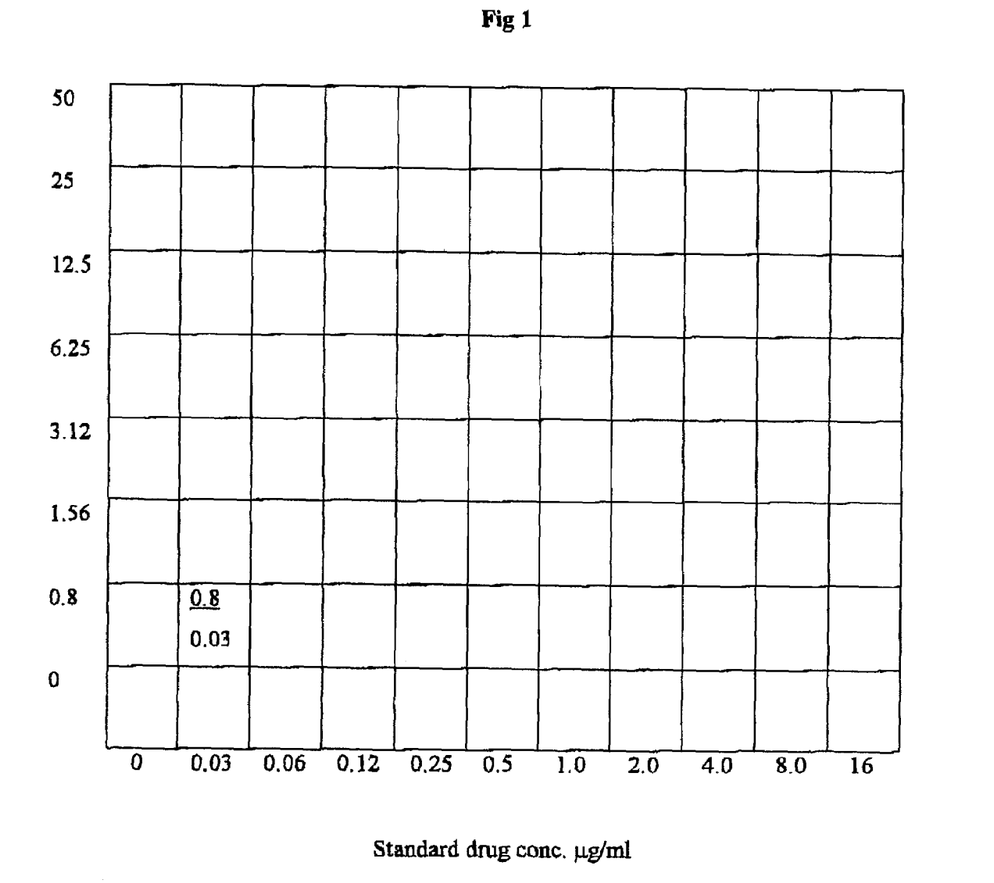
FIG. 1 is antimicrobial composition of the invention according to the checker board method.
Figure 2:
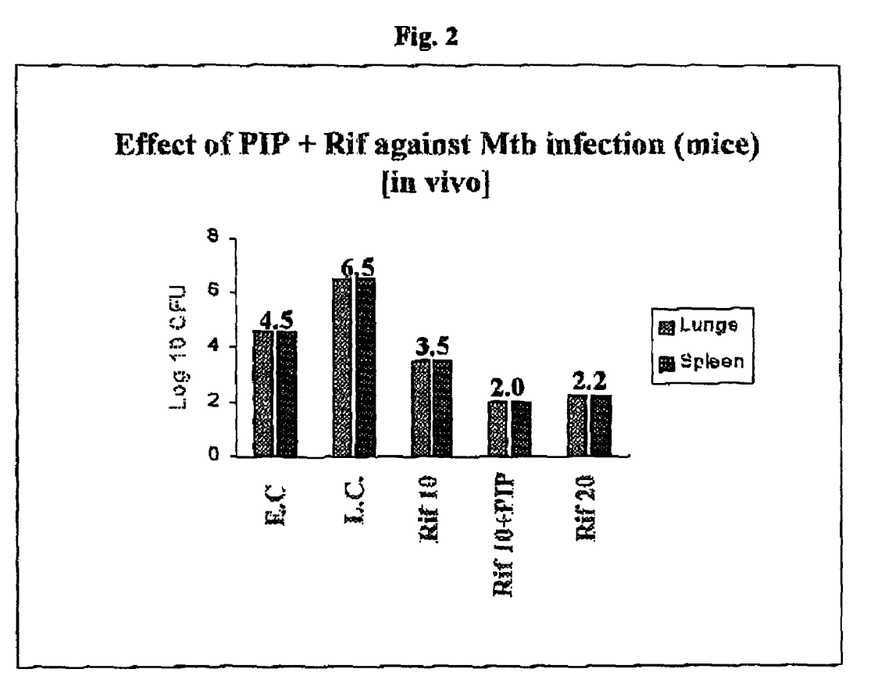
FIG. 2 is a graph showing the effect of rifampicin alone and in combination with piperine in an in vivo mice infection model.

The 'bioenhancer' refers to piperine (formula 1) or other such molecules, characterised fractions and/or extracts as a chemical entity. The process of obtaining piperine as more than 90% pure chemicaly characterized form has been disclosed in IP 172689, IP 172690, IP 176433, U.S. Pat. No. 5,439,891 and a co-pending U.S. patent application Ser. No. 60/306917/2001. The processes for preparation of a characterised fraction (HPLC profile enclosed) and a pure chemically characterised molecule (FIG. 2) from *Cuminum cyminum* have been disclosed in co-pending patent application No. NF 515/2001 (U.S. application Ser. No. 10/386,395, filed Mar. 11, 2003). The ratio of those two bioenhancers to drugs may vary from 1 to 50% for the fraction and from 0.1 to 30% for the pure molecule to obtain desired reduction in MIC values anti infectives. The ratios of the drug and the bioenhancers and/or in composite bioenhancers are governed by amounts sufficient to produce enhanced therapeutic efficacy as measured by MIC of the formulation being lesser than the drug alone. A pharmaceutical carrier is generally an inert bulk agent added to make the ingredients achieve superior admixing and can be solid or liquid. The inert parts of standard pharmaceutical compositions used in this process are also part of the present invention.

Study Design

Figure 3:
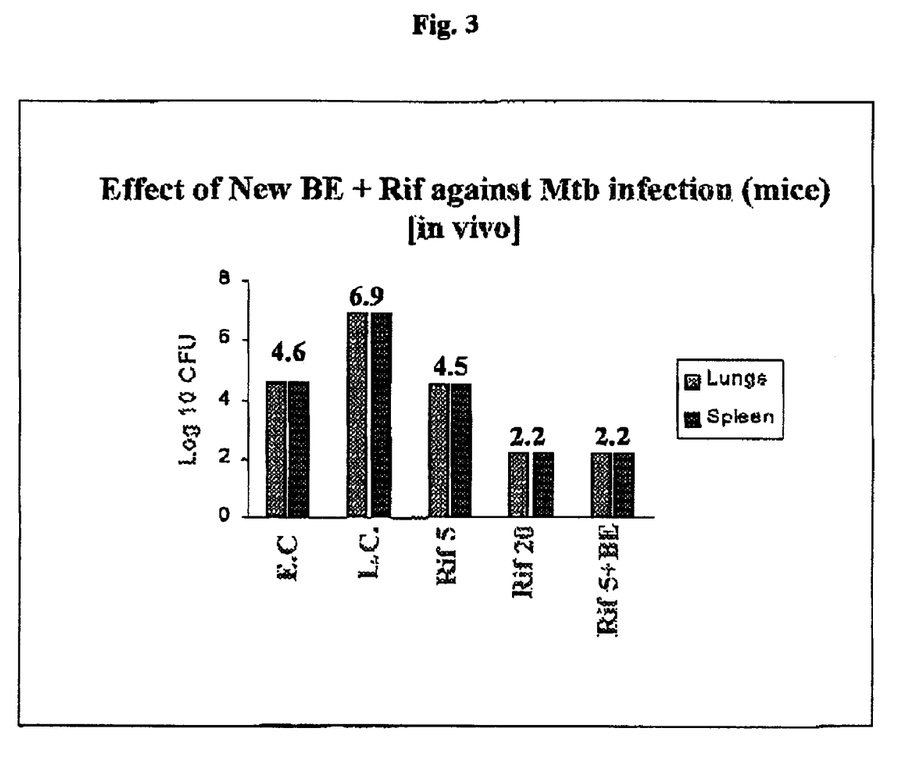
FIG. 3 is a graph showing the effect of rifampicin alone and in combination with 3',5-Dihydroxy flavone 7-O-β-D-galacturonide-4'-O-β-D-glucopyranoside of formula 2 in in vivo mice infection model.

The checkerboard method:

This is the most frequently used method to access the antimicrobial combinations in vitro. The term "checkerboard" refers to the pattern (of tubes or microtiter plate wells) formed by multiple dilutions of two drugs being tested (Eliopoulos G M, Moellering R C. Antimicrobila Combinations. In: Antibiotics in Laboratory Medicine: USA: Williams & Wilkins). In the present study the checkerboard consisted of columns in which each tube (or well) contains the same amount of the standard drug (antibacterial/antifungal/anti-TB/antiviral) being diluted along the x-axis and rows in which each tube (or well) contains the same amount of the bioenhancer being diluted on the y-axis (FIG. 3). As a result each square in the checkerboard (which represents one tube/well or plate) contained a unique combination of the standard drug and bioenhancer. The concentration range of standard drug in the present study was 64 µg/ml to 0.03 µg/ml, whereas the bioenhancer was tested in the range of 500 µg/ml to 0.2 µg/ml. This checkerboard technique can be performed with liquid or semisolid (agar) media.

Agar Method:

In this method the agar (Mueller Hinton agar, Middlebrook 7H10 agar) was autoclaved and allowed to cool to 50° C. to 55° C. The combination of the standard drug and the bioenhancer was added to the agar. Serial two fold dilutions of each of standard drug and the bioenhancer were prepared in appropriate solvents. In order to maintain the desired concentrations of both agar and drugs, and to rule out the effect of solvent, the volume of solvent (containing standard drug or bioenhancer) added to agar was kept small (i.e ≦5% of the total volume). After the agar plates have been poured and allowed to dry, the bacteria to be tested were applied to the surface of agar with a replicating device designed to deliver a standard inoculum (approx $10^4$ cfu/spot). The plates were incubated at 37° C. for 24 hrs (3 weeks in case of *Mycobacterium tuberculosis*)

Broth Method:

The above-mentioned checkerboard was also performed with liquid media in a microtiter plate format. This method was used to study the combination of antibacterial/antifingal/antiviral drugs with bioenhancer.

Inhibitory Effect of Bioenhancers

All bioenhancers were evaluated for their own inhibitory effect if any, at a concentration range of 500 µg/ml to 0.2 µg/ml. (Table 1, 2, & 3)

TABLE 1

Effect of Piperine on Microorganisms

| Organisms | Conc. of piperine µg/ml | | | | | |
|---|---|---|---|---|---|---|
| | 0.2 | 0.8 | 3.12 | 12.5 | 50 | 100 |
| *Staphylococcus aureus* ATCC 29313 | ++++ | ++++ | ++++ | ++++ | ++++ | +++ |
| Methicillin Resistant *Staphylococcus aureus* (MRSA) | ++++ | ++++ | ++++ | ++++ | ++++ | +++ |
| *Staphylococcus epidermidis* ATCC 12228 | ++++ | ++++ | ++++ | ++++ | +++ | ++ |
| *Staphylococcus hemolyticus* ATCC 29978 | ++++ | ++++ | ++++ | ++++ | +++ | ++ |
| *Bacillus cereus* RRL 02 | ++++ | ++++ | ++++ | ++++ | ++++ | ++++ |
| *Escherichia coli* ATCC 25922 | ++++ | ++++ | ++++ | ++++ | ++++ | ++++ |
| *Salmonella typhi* AIIMS 2 | ++++ | ++++ | ++++ | ++++ | ++++ | ++++ |
| *Klebsiella pneumoniae* ATCC 75388 | ++++ | ++++ | ++++ | ++++ | ++++ | ++++ |
| *Pseudomonas aeruginosa* ATCC 27583 | ++++ | ++++ | ++++ | ++++ | ++++ | ++++ |
| *Candida albicans* ATCC 90028 | ++++ | ++++ | ++++ | ++++ | ++++ | +++ |
| *Candida parapsilosis* ATCC 22019 | ++++ | ++++ | ++++ | ++++ | ++++ | +++ |
| *Candida glabrata* ATCC 90030 | ++++ | ++++ | ++++ | ++++ | ++++ | +++ |
| *Candida tropicalis* ATCC 750 | ++++ | ++++ | ++++ | ++++ | ++++ | +++ |
| *Candida krusei* ATCC 6258 | ++++ | ++++ | ++++ | ++++ | ++++ | +++ |
| *Aspergillus flavus* MTCC 1973 | ++++ | ++++ | ++++ | ++++ | +++ | ++ |
| *Aspergillus fumigatus* SI-1 | ++++ | ++++ | ++++ | ++++ | +++ | ++ |
| *Mycobacterium tuberculosis* $H_{37}Rv$ | ++++ | ++++ | ++++ | ++++ | ++++ | ++++ |
| *Mycobacterium tuberculosis* 615 | ++++ | ++++ | ++++ | ++++ | ++++ | ++++ |
| *Mycobacterium avium* ATCC 49601 | ++++ | ++++ | ++++ | ++++ | ++++ | ++++ |
| *Mycobacterium intracelluare* ATCC 13950 | ++++ | ++++ | ++++ | ++++ | ++++ | ++++ |

Methicillin Resistant *Staphylococcus aureus*
++++ No inhibition,
+++ 20% inhibition,
++ 50% inbibition

TABLE 2

Effect of fraction of *Cuminum cyminum* on Micro organisms

| | Conc. of fraction of *Cuminum cyminum* | | | | | |
|---|---|---|---|---|---|---|
| Organisms | 0.5 μg/ml | 2.0 μg/ml | 8.0 μg/ml | 31.2 μg/ml | 125 μg/ml | 500 μg/ml |
| *Staphylococcus aureus* ATCC 29313 | ++++ | ++++ | ++++ | ++++ | ++++ | ++++ |
| Methicillin Resistant *Staphylococcus aureus* (MRSA) | ++++ | ++++ | ++++ | ++++ | ++++ | ++++ |
| *Staphylococcus epidermidis* ATCC 12228 | ++++ | ++++ | ++++ | ++++ | ++++ | ++++ |
| *Staphylococcus. hemolyticus* ATCC 29978 | ++++ | ++++ | ++++ | ++++ | ++++ | ++++ |
| *Bacillus cereus* RRL 02 | ++++ | ++++ | ++++ | ++++ | ++++ | ++++ |
| *Escherichia coli* ATCC 25922 | ++++ | ++++ | ++++ | ++++ | ++++ | ++++ |
| *Salmonella typhi* AIIMS 2 | ++++ | ++++ | ++++ | ++++ | ++++ | ++++ |
| *Klebsiella pneumoniae* ATCC 75388 | ++++ | ++++ | ++++ | ++++ | ++++ | ++++ |
| *Pseudomonas aeruginosa* ATCC 27583 | ++++ | ++++ | ++++ | ++++ | ++++ | ++++ |
| *Candida albicans* ATCC 90028 | ++++ | ++++ | ++++ | ++++ | ++++ | ++++ |
| *Candida parapsilosis* ATCC 22019 | ++++ | ++++ | ++++ | ++++ | ++++ | ++++ |
| *Candida glabrata* ATCC 90030 | ++++ | ++++ | ++++ | ++++ | ++++ | ++++ |
| *Candida tropicalis* ATCC 750 | ++++ | ++++ | ++++ | ++++ | ++++ | ++++ |
| *Candida krusei* ATCC 6258 | ++++ | ++++ | ++++ | ++++ | ++++ | ++++ |
| *Aspergillus flavus* MTCC 1973 | ++++ | ++++ | ++++ | ++++ | ++++ | ++++ |
| *Aspergillus fumigatus* SI-1 | ++++ | ++++ | ++++ | ++++ | ++++ | ++++ |
| *Mycobacterium tuberculosis* $H_{37}Rv$ | ++++ | ++++ | ++++ | ++++ | ++++ | ++++ |
| *Mycobacterium tuberculosis* 615 | ++++ | ++++ | ++++ | ++++ | ++++ | ++++ |
| *Mycobacterium avium* ATCC 49601 | ++++ | ++++ | ++++ | ++++ | ++++ | ++++ |
| *Mycobacterium intracelluare* ATCC 13950 | ++++ | ++++ | ++++ | ++++ | ++++ | ++++ |

Methicillin Resistant *Staphylococcus aureus*
++++ No inhibition,
+++ 20% inhibition,
++ 50% inhibition

TABLE 3

Effect of pure molecule of *Cuminum cyminum* on Micro organisms

| | Conc. of pure molecule of *Cuminum cyminum* μg/ml | | | | | |
|---|---|---|---|---|---|---|
| Organisms | 0.2 | 0.8 | 3.12 | 12.5 | 50 | 100 |
| *Staphylococcus aureus* ATCC 29313 | ++++ | ++++ | ++++ | ++++ | ++++ | ++++ |
| Methicillin Resistant *Staphylococcus aureus* (MRSA) | ++++ | ++++ | ++++ | ++++ | ++++ | ++++ |
| *Staphylococcus epidermidis* ATCC 12228 | ++++ | ++++ | ++++ | ++++ | ++++ | ++++ |
| *Staphylococcus, hemolyticus* ATCC 29978 | ++++ | ++++ | ++++ | ++++ | ++++ | ++++ |
| *Bacillus cereus* RRL 02 | ++++ | ++++ | ++++ | ++++ | ++++ | ++++ |
| *Escherichia coli* ATCC 25922 | ++++ | ++++ | ++++ | ++++ | ++++ | ++++ |
| *Salmonella typhi* AIIMS 2 | ++++ | ++++ | ++++ | ++++ | ++++ | ++++ |
| *Klebsiella pneumoniae* ATCC 75388 | ++++ | ++++ | ++++ | ++++ | ++++ | ++++ |
| *Pseudomonas aeruginosa* ATCC 27583 | ++++ | ++++ | ++++ | ++++ | ++++ | ++++ |
| *Candida albicans* ATCC 90028 | ++++ | ++++ | ++++ | ++++ | ++++ | ++++ |
| *Candida parapsilosis* ATCC 22019 | ++++ | ++++ | ++++ | ++++ | ++++ | ++++ |
| *Candida glabrata* ATCC 90030 | ++++ | ++++ | ++++ | ++++ | ++++ | ++++ |
| *Candida tropicalis* ATCC 750 | ++++ | ++++ | ++++ | ++++ | ++++ | ++++ |
| *Candida krusei* ATCC 6258 | ++++ | ++++ | ++++ | ++++ | ++++ | ++++ |
| *Aspergillus flavus* MTCC 1973 | ++++ | ++++ | ++++ | ++++ | ++++ | ++++ |
| *Aspergillus fumigatus* SI-1 | ++++ | ++++ | ++++ | ++++ | ++++ | ++++ |
| *Mycobacterium tuberculosis* $H_{37}Rv$ | ++++ | ++++ | ++++ | ++++ | ++++ | ++++ |
| *Mycobacterium tuberculosis* 615 | ++++ | ++++ | ++++ | ++++ | ++++ | ++++ |
| *Mycobacterium avium* ATCC 49601 | ++++ | ++++ | ++++ | ++++ | ++++ | ++++ |
| *Mycobacterium intracelluare* ATCC 13950 | ++++ | ++++ | ++++ | ++++ | ++++ | ++++ |

Methicillin Resistant *Staphylococcus aureus*
++++ No inhibition,
+++ 20% inhibition,
++ 50% inhibition

EXAMPLES

The following examples are intended to demonstrate some of the preferred embodiments but in no way be construed so as to limit the scope of the invention. Any person skilled in the art can design more formulations, which may be considered as part of the present invention.

Example 1

Preparation of Colourless, Non-pungent 99% Pure Piperine

This was done by the process claimed in Indian Patents 1726891 and IP 172690 and U.S. Pat. No. 5,439,891 and U.S. application Ser. No, 60/306917/2001, which is incorporated herein by reference.

Example 2

Decrease in the MICs of Rifampicin Against *M.tuberculosis, M. avium* and *M. intracellure* When Used in Combination with Piperine and Fraction of *Cuminum cyminum*

Minimum Inhibitory Concentration (MIC) of rifampicin alone and in combination with piperine was performed against Mycobacterial species, using method described in the study design.

Two-fold reduction in MIC of rifampicin was observed in combination with piperine and fraction of *Cuminum cyminum* (Table 4-a, 4-b)

Example 3

Reduction in the Dose Requirement of Rifampicin When Used in Combination with Piperine and Fraction of *Cuminum cyminum* in Systemic Infection Model of Mice The study was conducted to see the in vivo response of rifampicin in combination with piperine. The Swiss albino mice were infected intravenously with *M.tuberculosis* $H_{37}Rv$ ($10^6$ CFU/mouse). The infected mice were divided in groups and each group consisted of 6 mice.

The treatment started 24 hrs post infection and continued for 4 weeks in once a day for 5 days in a week dosing schedule. The mice were sacrificed after 4 weeks and the CFU was enumerated from the lungs and the spleen. Rifampicin alone at 20 mg/kg was able to bring about 2-log deduction in log 10 CFU. Same effect was observed with rifampicin at 10 mg/kg when given in combination with pipette at 20 mg/kg. Whereas fraction of *Cuminum cyminum* was more effective as it yielded the same reduction in log 10 CFU at 5 mg/kg dose of rifampicin. (FIGS. 4-*a*, 4-*b*)

TABLE 4-a

MICs of Rifampicin alone and in combination with piperine

| | | MIC (µg/ml) | | | |
|---|---|---|---|---|---|
| S.No | Organisms | Rif | Rif + 0.09 µg/ml | Rif + 0.78 µg/ml | Rif + 6.25 µg/ml | Rif + 50 µg/ml |
| 1. | M tuberculosis $H_{37}Rv$ | 0.12 | 0.03 | 0.03 | 0.06 | 0.12 |
| 2. | M tuberculosis 611 | 0.06 | 0.03 | 0.03 | 0.03 | 0.03 |
| 3. | M tuberculosis 615 | 0.06 | 0.03 | 0.03 | 0.03 | 0.03 |
| 4. | M tuberculosis 616 | 0.12 | 0.06 | 0.03 | 0.03 | 0.03 |
| 5. | M avium ATCC 49601 | 2.0 | 0.5 | 0.5 | 0.5 | 0.5 |
| 6. | M intracellure ATCC 13950 | 2.0 | 2.0 | 1.0 | 1.0 | 1.0 |

TABLE 4-b

MICs of Rifampicin alone and in combination with fraction of *Cuminum cyminum*.

| | | MIC (µg/ml) | | | |
|---|---|---|---|---|---|
| S.No | Organisms | Rif | Rif + 0.09 µg/ml | Rif + 0.78 µg/ml | Rif + 6.25 µg/ml | Rif + 50 µg/ml |
| 1. | M tuberculosis $H_{37}Rv$ | 0.12 | 0.03 | 0.03 | 0.03 | 0.03 |
| 2. | M tuberculosis 611 | 0.06 | 0.03 | 0.03 | 0.03 | 0.03 |
| 3. | M tuberculosis 615 | 0.06 | 0.03 | 0.03 | 0.03 | 0.03 |
| 4. | M tuberculosis 616 | 0.12 | 0.06 | 0.06 | 0.06 | 0.06 |
| 5. | M avium ATCC 49601 | 2.0 | 1.0 | 1.0 | 0.1 | 1.0 |
| 6. | M intracellure ATCC 13950 | 2.0 | 1.0 | 1.0 | 1.0 | 1.0 |

Example 4

Decrease in the MICs of Ciprofloxacin Against *Staphylococcus aureus*, MRSA and *Staphylococcus hemolyticus* When Used in Combination with Piperine Minimum Inhibitory Concentration (MIC) of ciprofloxacin alone and in combination with piperine was performed against bacterial species, using method described in the study design. Two to more than eight fold reductions in MIC of ciprofloxacin was observed in combination with piperine. (Table-5)

TABLE 5

MICs of Ciprofloxacin alone and in combination with piperine.

| | | MIC (µg/ml) | | | |
|---|---|---|---|---|---|
| S. No | Organisms | Cipro | Cipro + P- 12.5 µg/ml | Cipro + P- 50 µg/ml | Cipro + P- 100 µg/ml |
| 1. | S aureus ATCC 29313 | 0.5 | 0.25 | 0.25 | 0.06 |
| 2. | MRSA 450 | 64 | 64 | 32 | 16 |
| 3. | MRSA 15187 | 64 | 32 | 16 | 8 |
| 4. | S epidermidis ATCC 12228 | 0.25 | 0.25 | <0.03 | <0.03 |
| 5. | S hemolyticus ATCC 29978 | 0.25 | 0.12 | 0.12 | <0.03 |

Example 5

Decrease in the MICs of Fluconazole Against *Candida albicans*, *Candida parapsilosis* and *Candida glabrata* When Used in Combination with Piperine Minimum Inhibitory Concentration (MIC) of fluconazole alone and in combination with piperine was performed against fungal species, using method described in the study design Two to eight fold reductions in MIC of fluconazole was observed in combination with piperine. (Table-6)

TABLE 6

MICs of Fluconazole alone and in combination with piperine (P)

| Fungal Cultures | MIC (µg/ml) | | | | | |
|---|---|---|---|---|---|---|
| | FCZ | FCZ + P 1.56 µg/ml | FCZ + P 6.25 µg/ml | FCZ + P 12.5 µg/ml | FCZ + P 25 µg/ml | FCZ + P 50 µg/ml |
| Candida albicans A261 | 2.0 | 2.0 | 2.0 | 2.0 | 2.0 | 1.0 |
| Candida albicans ATCC 90028 | 0.5 | 1.0 | 0.5 | 0.25 | 0.25 | <0.12 |
| Candida parapsilosis ATCC 22019 | 16 | 16 | 16 | 8.0 | 2.0 | 1.0 |
| Candida glabrata ATCC 90030 | 16 | 16 | 16 | 4.0 | 2.0 | 1.0 |

Example 6

List of Drugs Cited in Accompanying Table 7 as Some of the Examples for the Purpose of the Present Invention

REFERENCES

1. Gutman L T. The use of TMP-SMX in children: a review of adverse reactions and indications. Pediatr Infect Dis 1984;3:349–57.
2. Bushby S R M. Synergy of trimethoprim and sulfonamides: History and current status. In: Antibiotics and Antibiosis in Agriculture, London: Butterworths. 1977; 64–81.
3. Olin B R, ed. Drug Facts and Comparisons. St. Louis, Facts and Comparisons, Inc.; 1998: 408b–409d.
4. Cockerill F R, Edson R S. TMP-SMX. Mayo Clin Proc 1991;66:1260–9.

TABLE 7

| | | MIC (µg/ml) | | | | | | | | |
|---|---|---|---|---|---|---|---|---|---|---|
| | | Piperine | | | Pure molecule of *C. cyminum* | | | Fraction of *C. cyminum* | | |
| Drugs | Organisms | Drug alone | Drug + BE | % decrease | Drug alone | Drug + BE | % decrease | Drug alone | Drug + BE | % decrease |
| Fluroquinolones | | | | | | | | | | |
| Ciprofloxacin | Gram positive bacteria | 0.12–32 | 0.06–8 | 50–76 | 0.12–32 | 0.06–8 | 50–76 | 0.12–32 | 0.12–16 | 0–50 |
| | Gram negative bacteria | 0.03–0.5 | 0.03–0.25 | 0–50 | 0.03–0.5 | 0.03–0.12 | 0–76 | 0.03–0.5 | 0.03–0.25 | 0–50 |
| | M. tuberculosis | 0.5–1 | 0.25–0.5 | 50 | 0.5–1 | 0.25–0.5 | 50 | 0.5–1 | 0.5–1 | 0 |
| Ofloxacin | Gram positive bacteria | 0.12–32 | 0.06–8 | 50–76 | 0.12–32 | 0.06–8 | 50–76 | 0.12–32 | 0.12–32 | 0 |
| | Gram negative bacteria | 0.06–32 | 0.03–16 | 50 | 0.06–32 | 0.03–16 | 50 | 0.06–32 | 0.06–32 | 0 |
| | M. tuberculosis | 0.5–2.5 | 0.5–1.25 | 0–50 | 0.5–25 | 0.5–1.25 | 0–50 | 0.5–2.5 | 0.5–2.5 | 0 |
| Norfloxacin | Gram positive bacteria | 0.12–32 | 0.06–4 | 50–97 | 0.12–32 | 0.06–8 | 50–76 | 0.12–32 | 0.12–32 | 0 |
| | Gram negative bacteria | 0.03–64 | 0.03–32 | 0–50 | 0.03–64 | 0.03–64 | 0 | 0.03–64 | 0.03–64 | 0 |
| Cephalosporins | | | | | | | | | | |
| Cefaclor | Gram positive bacteria | 0.06–32 | 0.03–16 | 50 | 0.06–32 | 0.06–32 | 0 | 0.06–32 | 0.06–16 | 0–50 |
| | Gram negative bacteria | 0.25–64 | 0.25–32 | 0–50 | 0.25–64 | 0.25–64 | 0 | 0.25–64 | 0.25–32 | 0–50 |
| Cefdinir | Gram positive bacteria | 0.06–32 | 0.06–32 | 0 | 0.06–32 | 0.06–32 | 0 | 0.06–32 | 0.03–16 | 50 |
| | Gram negative bacteria | 0.25–64 | 0.25–64 | 0 | 0.25–64 | 0.25–64 | 0 | 0.25–64 | 0.12–32 | 50 |
| Ceftrioxone | Gram positive bacteria | 0.12–32 | 0.06–8 | 50–76 | 0.12–32 | 0.12–16 | 0–50 | 0.12–32 | 0.06–8 | 50–76 |
| | Gram negative bacteria | 0.03–32 | 0.03–16 | 0–50 | 0.03–32 | 0.03–16 | 0–50 | 0.03–32 | 0.01–8 | 50–76 |
| Cefpedoxime | Gram positive bacteria | 0.12–16 | 0.06–8 | 50 | 0.12–16 | 0.12–8 | 0–50 | 0.12–16 | 0.06–8 | 50–76 |
| | Gram negative bacteria | 0.03–64 | 0.03–32 | 50 | 0.03–64 | 0.03–32 | 0–50 | 0.03–64 | 0.01–32 | 50–76 |
| Aminoglycosides | | | | | | | | | | |
| Amikacin | Gram positive bacteria | 2–32 | 2–16 | 0–50 | 2–32 | 1–16 | 50 | 2–32 | 2–16 | 0–50 |
| | Gram negative bacteria | 0.12–4 | 0.06–2 | 50 | 0.12–4 | 0.06–2 | 50 | 0.12–4 | 0.06–2 | 50 |
| | M. tuberculosis | 0.5–1 | 0.25–0.5 | 50 | 0.5–1 | 0.5–0.5 | 0–50 | 0.5–1 | 0.5–0.5 | 0–50 |
| | Gram positive bacteria | | | | | | | | | |
| | Gram negative bacteria | 0.004–64 | 0.004–64 | 0 | 0.004–64 | 0.004–16 | 0–76 | 0.004–64 | 0.004–16 | 0–76 |
| Anti TB | | | | | | | | | | |
| Isoniazid | M. tuberculosis | 0.12–32 | 0.06–8 | 50–76 | 0.12–32 | 0.06–16 | 50 | 0.12–32 | 0.12–32 | 0 |
| Rifampicin | M. tuberculosis | 0.06–0.5 | 0.03–0.1 | 50–76 | 0.06–0.5 | 0.01–0.12 | 76 | 0.06–0.5 | 0.01–0.12 | 76 |
| Pyrazinamide | M. tuberculosis | 6–60 | 6–30 | 0–50 | 6–60 | 3–30 | 50–76 | 6–60 | 3–30 | 50–76 |
| Ethambutol | M. tuberculosis | 1–5 | 1–0.25 | 0–50 | 1–5 | 1–5 | 0 | 1–5 | 1–5 | 0 |

TABLE 7-continued

| | | MIC (µg/ml) | | | | | | | | |
|---|---|---|---|---|---|---|---|---|---|---|
| | | Piperine | | | Pure molecule of *C. cyminum* | | | Fraction of *C. cyminum* | | |
| Drugs | Organisms | Drug alone | Drug + BE | % decrease | Drug alone | Drug + BE | % decrease | Drug alone | Drug + BE | % decrease |
| Glycopeptides | | | | | | | | | | |
| Vancomycin | Gram positive bacteria | 0.03–8 | 0.01–4 | 50 | 0.03–8 | 0.03–8 | 0 | 0.03–8 | 0.03–8 | 0 |
| Anti fungal | | | | | | | | | | |
| Fluconazole | Yeast | 0.12–64 | 0.06–32 | 50 | 0.12–64 | 0.12–64 | 0 | 0.12–64 | 0.12–64 | 0 |
| Ketoconazole | Yeast | 0.12–0.5 | 0.12–0.25 | 0–50 | 0.12–0.5 | 0.06–0.12 | 50–76 | 0.12–0.5 | 0.12–0.25 | 50 |
| | Filamentous fungi | 0.25–2 | 0.25–2 | 0 | 0.25–2 | 0.12–1 | 50 | 0.25–2 | 0.25–2 | 0 |
| Amphotericin B | Yeast | 0.25–2.0 | 0.12–1 | 50 | 0.25–2.0 | 0.12–0.5 | 50–76 | 0.25–2.0 | 0.12–0.5 | 50–76 |
| | Filamentous fungi | 0.25–4 | 0.25–2 | 0–50 | 0.25–4 | 0.12–2 | 50 | 0.25–4 | 0.12–2 | 50 |

We claim:

1. A composition comprising a mixture of an anti-infective agent and a potentiator comprising a 3',5-dihydroxy flavone 7-O-β-D-galacturonide-4'-O-β-D-glucopyranoside compound of formula 2 in pure form or in the form of a HPLC fingerprinted fraction of 3',5-dihydroxy flavone 7-O-β-D-galacturonide-4'-O-β-D-glucopyranoside from *Cuminum cyminum* said potentiator optionally also comprising a piperine compound of formula 1:

Formula 1

Formula 2 said potentiator being present in the composition in an amount effective to potentiate the effectiveness of the anti-infective agent against a microorganism such that the composition has an increased bioefficacy against the microorganisms than does the composition without the potentiator.

2. A composition as claimed in claim 1, wherein the anti-infective agent is selected from the group consisting of penicillins, cephalosporins, aminoglycosides, glycopeptides, fluoroquinolones, macrolides, tetracyclines, first and second line anti-TB drugs, antileprosy drugs, oxazolidelones, antifungal agents, antiviral agents and pyrimidine derivative—sulphonamine combinations.

3. A composition as claimed in claim 1, wherein the anti-infective agent is an anti-fungal agent selected from the group consisting of polyenes, imidazoles and triazoles.

4. A composition as claimed in claim 1, wherein the anti-infective agent is an antiviral agent selected from the group consisting of zidovudines, idouridine, acyclovir and ribavarine.

5. A composition as claimed in claim 1, wherein the composition has a bioefficacy against the microorganism that is equivalent to the bioefficacy of a composition without the potentiator having a concentration of the anti-infective agent that is two to eight times greater than the concentration of the anti infective agent in the composition with the potentiator.

6. A composition as claimed in claim 1, wherein the composition includes one or more pharmaceutically acceptable additives and excipients.

7. A composition as claimed in claim 6, wherein the additives and excipients comprise nutrients, proteins, carbohydrates, sugar, talc, magnesium stearate, cellulose, calcium carbonate, starch-gelatin paste, pharmaceutically acceptable carriers, diluents and/or solvents.

8. A composition as claimed in claim 1, wherein the composition is in oral administration form.

9. A composition as claimed in claim 1, wherein the ratio of the anti-infective agent to the potentiator is in the range of 1:1 to 1:5.

10. A composition as claimed in claim 6, wherein the additives have no effect on an anti-infective property of the composition.

11. A composition as claimed in claim 1, wherein the potentiator comprises the piperine compound of formula 1 admixed with the compound of formula 2.

12. A composition as claimed in claim 1, wherein the potentiator does not contain the piperine compound.

13. A process for the preparation of the composition of claim 1, comprising a step of physically admixing the anti-infective agent with the potentiator.

14. A process as claimed in claim 13, wherein the physical admixing comprises admixing by dialysis, by molecular sieving or by membranes.

15. A process as claimed in claim 13, wherein the process comprises mixing the potentiator with water, alcohol, combinations of water and alcohol, hydrocarbons ketones or ethers.

16. A process as claimed in claim 13, wherein the potentiator comprises the compound of formula 2 and the piperine compound of formula 1 and the anti infective agent is selected from the group consisting of penicillins, cephalosporins, aminoglycosides, glycopeptides, fluroquinolones, macrolides, tetracyclines, first and second line anti-TB drugs, antileprosy drugs, oxazolidelones, antifungal agents, antiviral agents and pyrimidine derivative—sulphonamide combinations.

17. A process as claimed in claim 16, wherein the anti-infective agent comprises an anti-fungal agent comprising polyenes, imidazoles or triazoles.

18. A process as claimed in claim 16, wherein the anti-infective agent comprises an antiviral agent selected from the group consisting of Zidovudines, idouridine, acyclovir and ribavarine.

19. A process as claimed in claim 13, wherein the potentiator is a 3',5-dihydroxy flavone 7-O-β-D-galacturonide-4'-O-β-D-glucopyranoside compound admixed with the anti-infective agent in pure form.

20. A composition as claimed in claim 12, wherein the potentiator is a compound of formula 2 prepared by subjecting *Cuminum cyminum* to high pressure liquid chromatagraphy to form a HPLC fingerprinted fraction of 3',5-dihydroxy flavone 7-O-β-D-galacturonide-4'-O-β-D-glucopyranoside from the *Cuminum cyminum*.

21. A process as claimed in claim 16, wherein the composition has a bioefficacy against the microorganism that is equivalent to the bioefficacy of a composition without the potentiator having a concentration of the anti-infective agent that is two to eight times greater than the concentration of the anti-infective agent in the composition with the potentiator.

22. A process as claimed in claim 16, wherein the admixing step comprises admixing one or more pharmaceutically acceptable additives and excipients with the anti-infective agent and potentiator.

23. A process as claimed in claim 22, wherein the additives and excipients comprise nutrients, proteins, carbohydrates, sugar, talc, magnesium stearate, cellulose, calcium carbonate, starch-gelatin paste, pharmaceutically acceptable carriers, diluents and/or solvents.

24. A process as claimed in claim 13, wherein the ratio of the anti-infective agent to the potentiator in the admixing step is in the range of 1:1 to 1:5.

25. A composition as claimed in claim 1, wherein the fraction consists essentially of the compound of formula 2.

26. A compositions as claimed in claim 1, wherein the fraction is an HPLC fingerprinted fraction from *Cuminum cyminum*.

* * * * *